US00PP21999P2

(12) United States Plant Patent
Probst

(10) Patent No.: US PP21,999 P2
(45) Date of Patent: Jun. 28, 2011

(54) ***COREOPSIS* PLANT NAMED 'GALAXY'**

(50) Latin Name: ***Coreopsis* hybrid**
Varietal Denomination: Galaxy

(76) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 12/658,194

(22) Filed: Feb. 4, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — Kent L Bell
(74) *Attorney, Agent, or Firm* — Penny J. Aguirre

(57) ABSTRACT

A new cultivar of hybrid *Coreopsis* named 'Galaxy' characterized its inflorescences with semi-double ray florets that are solid yellow in color and held just above the foliage, its compact plant habit, its healthy and vigorous growth habit, and its perennial plant habit and cold hardiness to least U.S.D.A. Zone 5.

2 Drawing Sheets

Botanical classification: *Coreopsis* hybrid.
Variety denomination: 'Galaxy'.

CROSS REFERENCE TO A RELATED APPLICATION

This application is co-pending with a U.S. Plant Patent Application filed for a plant derived from the same cross in the Inventor's breeding program that is entitled *Coreopsis* Plant Named 'Cosmic Eye' (U.S. Plant patent application Ser. No. 12/657,956).

BACKGROUND OF THE INVENTION

The present invention relates to a new and distinct cultivar of *Coreopsis* plant, botanically of hybrid origin and known as *Coreopsis* 'Galaxy' and will be referred to hereinafter by its cultivar name, 'Galaxy'. The new cultivar of *Coreopsis* is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of inflorescence colors and plant forms. The inventor collected seed in the wild from five different species that are not commercialized and made six generations of crosses to produced interspecific hybrids to utilize in his breeding work.

The Inventor made a controlled cross in September of 2006 in his test garden in Hubbardston, Mass. between an unnamed sibling of *Coreopsis* 'Redshift' (U.S. Plant Pat. No. 20,412) as the female parent and an unnamed sibling of *Coreopsis* 'Full Moon' (U.S. Plant Pat. No. 19,364) as the male parent. 'Galaxy' was selected in summer 2007 as a single unique plant amongst the resulting seedlings.

Asexual reproduction of the new cultivar was first accomplished by stem cuttings in Hubbardston, Mass. in August of 2007 by the Inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Galaxy' as unique from all *Coreopsis* cultivars and species known to the Inventor.

1. 'Galaxy' exhibits composite inflorescences with semi-double ray florets that are solid yellow in color.
2. 'Galaxy' exhibits inflorescences that are held just above the foliage.
3. 'Galaxy' exhibits a compact plant habit; reaching 30 to 45 cm in height (12 to 18 inches).
4. 'Galaxy' blooms from June until frost in Massachusetts.
5. 'Galaxy' exhibits a vigorous and healthy growth habit.
6. 'Galaxy' exhibits a reliable perennial habit and is cold hardy at least to U.S.D.A. Zone 5. The female parent differs from 'Galaxy' in having much taller plant height (reaching 3 feet in height) and in having inflorescences with a single row of ray florets that are pale yellow in color with red streaks. The male parent differs from 'Galaxy' in being taller in plant height (reaching about 2 feet in height) and in having inflorescences with ray florets that are single and solid light yellow in color. 'Galaxy' can be compared to *Coreopsis grandiflora* 'Sundancer' (U.S. Plant Pat. No. 7,823) and *Coreopsis* 'Full Moon'. 'Sundancer' is similar to 'Galaxy' in having inflorescences with double ray florets and a compact plant habit, however 'Sundancer' differs from 'Galaxy' in having ray florets that are gold in color. 'Full Moon' differs from 'Galaxy' in being taller in plant height and in having inflorescences with a single row of ray florets.

BRIEF DESCRIPTION OF THE DRAWING

The accompanying colored photographs illustrate the overall appearance and distinct characteristics of the new *Coreopsis*. The photographs were taken of a one year-old plant of 'Galaxy' grown in a garden in Mount Vernon, Wash.

The photograph in FIG. 1 shows a top perspective of 'Galaxy' in bloom.

Figure 1:
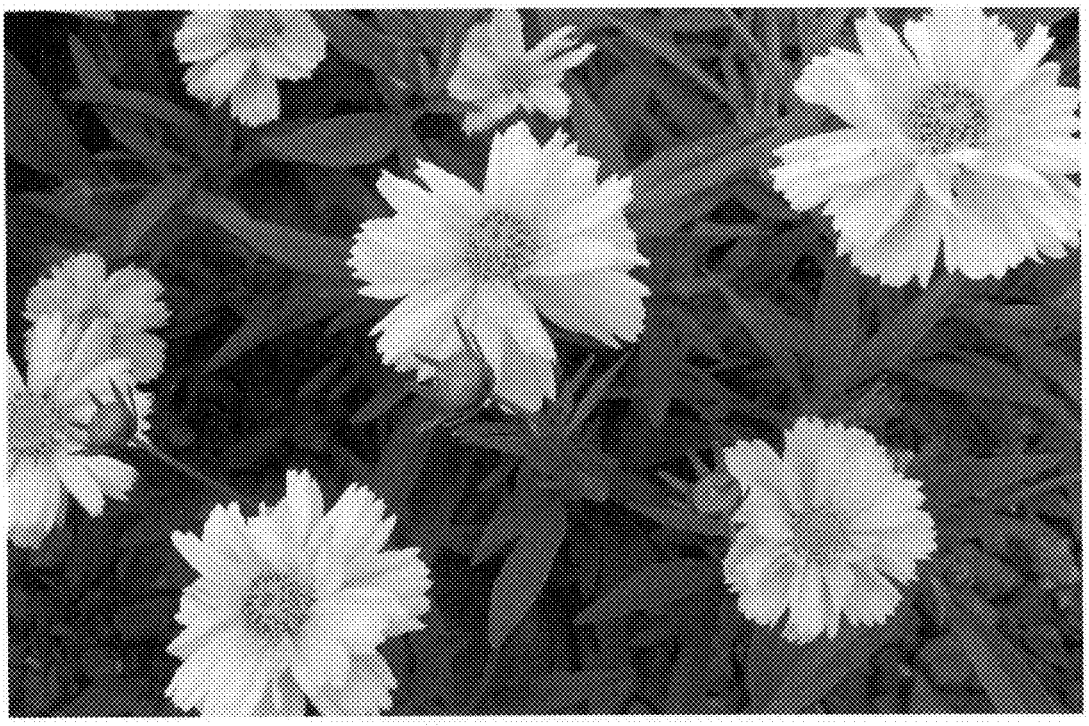
Figure 2:
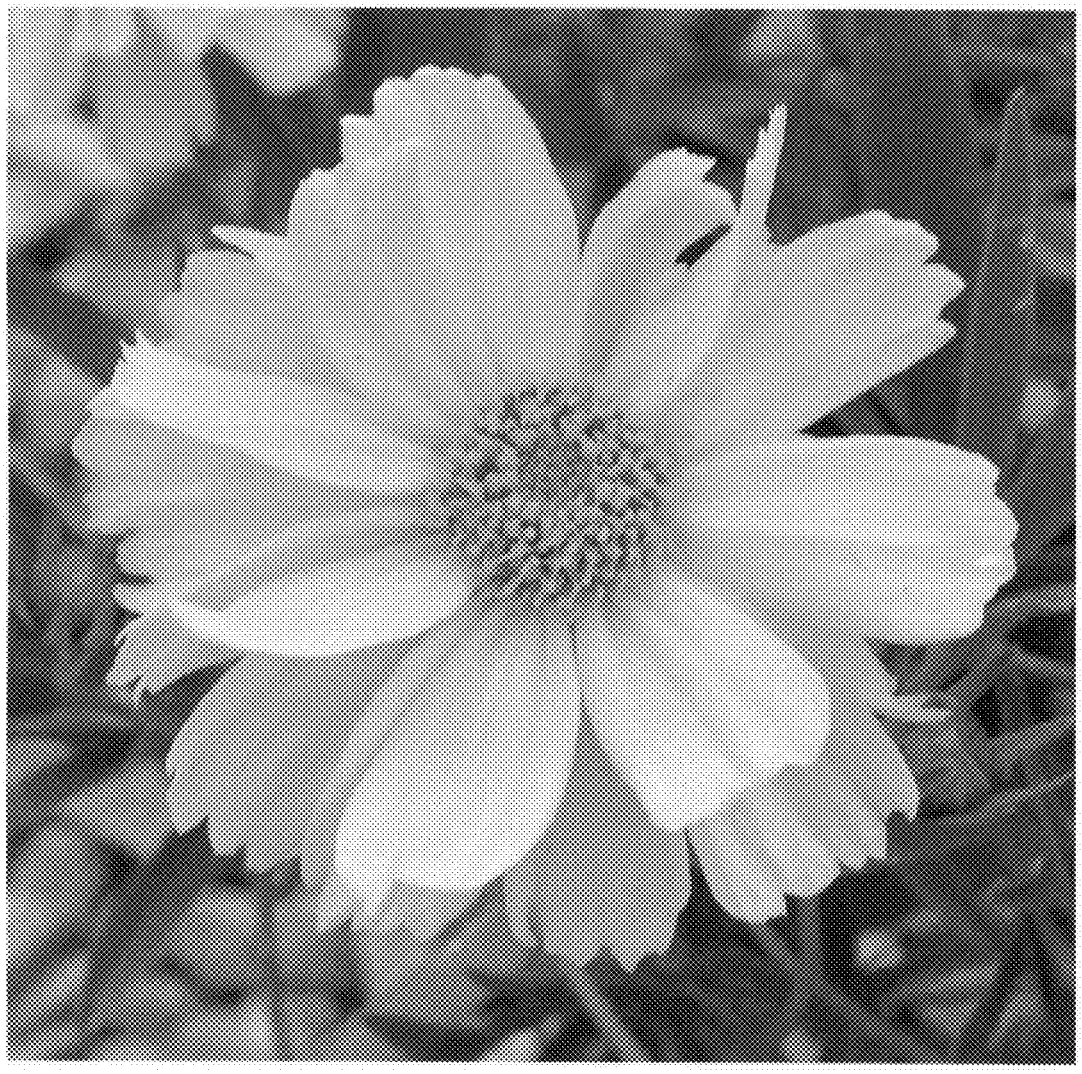

The photograph in FIG. 2 provides a close-up view of an inflorescence of 'Galaxy'. The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for two years in a trail garden in Hubbardston, Mass. with the detailed botanical data collected from six month-old plants of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from June until frost in central Massachusetts.

*Plant habit.*—Herbaceous perennial, clump-forming, compact, canopy upright and spreading.

*Height and spread.*—Reaches 35 to 40 cm (12 to 18 inches) in height and width.

*Cold hardiness.*—At least to U.S.D.A. Zone 5.

*Diseases resistance.*—Relatively disease resistant with no particular resistance to specific diseases observed.

*Root description.*—Fibrous, fine and well-branched.

Growth and propagation:

*Propagation.*—Terminal stem cuttings and division.

*Growth rate.*—Vigorous but retaining a compact habit.

Stem description:

*Shape.*—Oval, solid.

*Stem color.*—144A.

*Stem size.*—Main stem averages 20 cm in length and 3 mm in width with laterals variable in length and an average of 6 cm in length (excluding peduncles) and 2 mm in width.

*Stem surface.*—Very finely puberulent when young, ridged and finely puberulent when mature.

*Branching habit.*—An average of 3 basal branches with 4 secondary branches, branch internode is variable but typically about 5 cm and arise opposite at nodes.

Foliage description:

*Leaf division.*—Simple.

*Leaf margins.*—Entire with slight undulations.

*Leaf size.*—Variable, an average of 7.5 cm in length and 1.5 cm in width.

*Leaf shape.*—Lanceolate to gladiate (narrowly elliptic).

*Leaf base.*—Attenuate.

*Leaf apex.*—Narrowly acute.

*Leaf venation.*—Pinnate, not prominent, coloration same as leaf on both surfaces with the basal portion of mid rib on upper surface 144A.

*Leaf attachment.*—Sessile.

*Leaf arrangement.*—Opposite.

*Leaf surface.*—Dull and very finely puberulent on upper surface and dull and puberulent on lower surface.

*Leaf color.*—Young and mature upper surface; 137A, young and mature lower surface; 137B.

Flower description:

*Inflorescence type.*—Composite with semi-double ray florets surrounding disk florets in the center, forming a radiant head, inflorescences are borne on terminals arising from leaf axils.

*Lastingness of inflorescence.*—About one week until senescence of ray flowers, bracts and disk flowers are persistent.

*Fragrance.*—None detected.

*Quantity of inflorescences.*—An average of 5 per lateral branch, an average of 40 per plant grown in a one-gallon container.

*Inflorescence size.*—An average of 1.8 cm in depth and up to 4.8 cm in diameter with disk portion an average of 1.2 cm in diameter.

*Inflorescence buds.*—Average of 1.1 cm in depth and diameter, shape is spherical, a blend of 1A and 2A in color surrounded with bracts 137B in color.

*Peduncle.*—Strong, an average of 11 cm in length and 1.7 mm in diameter, 138A in color, glabrous surface with fine ridges.

Involucral bracts:

*Bract number.*—Two rows of 8.

*Bract arrangement.*—Outer bracts are un-fused and somewhat reflexed when inflorescence is fully open and becoming horizontal after ray florets drop, inner bracts overlap and surround receptacle with a campanulate form with apical portion unfused, spreading, and held close to lower surface of ray florets.

*Bract size.*—Outer bracts; up to 1.1 cm in length and 2 mm in width, inner bracts; up to 1.1 cm in length and 4 mm in width with free portion an average of 7 mm in length and 4 mm in width.

*Bract color.*—Outer bracts; 137B in both surfaces, inner bracts; 146A with apex and margin N144A.

*Bract texture.*—Waxy on outer and inner bracts.

*Bract apex.*—Acute on outer and inner bracts.

*Bract base.*—Truncate on inner and outer bracts.

*Bract margins.*—Entire with fine short stiff hairs on apex of outer bracts.

*Bract shape.*—Outer bracts; lanceolate, inner bracts; free portion broadly lanceolate.

Ray florets (sterile):

*Number.*—An average of 18 arranged primarily in two alternating rows.

*Shape.*—Broadly oblong with the appearance of three longitudinal sections with center section wider.

*Size.*—An average of 1.8 cm in length and 1 cm in width.

*Apex.*—3-noticed with center lobe emarginate and side lobes acute.

*Base.*—Broadly cuneate.

*Margins.*—Entire on sides, notched at apex.

*Aspect.*—Held primarily horizontal.

*Texture.*—Glabrous on upper and lower surfaces.

*Color.*—Upper and lower surface when opening and mature; 2A and lightly suffused with 7A near base.

Disk flowers (perfect):

*Shape.*—Tubular, corolla is fused, flared at apex.

*Number.*—About 200.

*Size.*—About 7 mm in length and 2 mm in width.

*Color.*—En masse; 17A when fully open and becoming a blend of 200C and N199B when dried and ray florets drop, corolla; base (tube) is 1C in color, flared portion is 17A and translucent.

*Receptacle.*—About 3.5 mm in diameter and 2 mm in depth, 150D in color.

Reproductive organs:

*Presence.*—Disk flowers are perfect, ray flowers are sterile.

*Gynoecium.*—1 Pistil, 5 mm in length, style is very fine and about 1C in color and translucent, bifid pilose stigma is 17A in color with branches about 1 mm in length and recurved, ovary is 1.5 mm in length, 1 mm in width, inferior, and 147C in color.

*Androecium.*—5 stamens, fused into tube surrounding style, 2 mm in length and 0.7 mm in width, about 165A in color, no pollen was observed.

*Fruit/seed.*—No fruit or seed development was observed.

It is claimed:

1. A new and distinct cultivar of *Coreopsis* plant named 'Galaxy' as herein illustrated and described.

* * * * *